(12) United States Patent
Yeung et al.

(10) Patent No.: US 7,497,937 B2
(45) Date of Patent: Mar. 3, 2009

(54) MICROFABRICATED CHIP AND METHOD OF USE

(75) Inventors: Edward S. Yeung, Ames, IA (US);
Ho-Ming Pang, Ames, IA (US); Futian Han, Ames, IA (US)

(73) Assignee: Combisep, Inc., Ames, IA (US)

( * ) Notice: Subject to any disclaimer, the term of this patent is extended or adjusted under 35 U.S.C. 154(b) by 866 days.

(21) Appl. No.: 10/934,259

(22) Filed: Sep. 3, 2004

(65) Prior Publication Data

US 2006/0049051 A1    Mar. 9, 2006

(51) Int. Cl.
    *G01N 27/453*    (2006.01)
(52) U.S. Cl. .................................. 204/603; 204/601
(58) Field of Classification Search ......... 204/451–455, 204/601–605, 610, 459
See application file for complete search history.

(56) References Cited

U.S. PATENT DOCUMENTS

| | | | |
|---|---|---|---|
| 4,417,967 A * | 11/1983 | Ledley | 204/466 |
| 4,874,490 A * | 10/1989 | Hochstrasser | 204/467 |
| 5,948,227 A | 9/1999 | Dubrow | |
| 5,989,402 A | 11/1999 | Chow | |
| 6,306,273 B1 | 10/2001 | Wainright | |
| 7,294,247 B1 * | 11/2007 | Tian et al. | 204/451 |
| 2002/0170825 A1 | 11/2002 | Lee | |

FOREIGN PATENT DOCUMENTS

| | | | |
|---|---|---|---|
| JP | 05-93711 A * | 4/1993 | |
| WO | WO 01/18528 A1 | 3/2001 | |

OTHER PUBLICATIONS

JPO English language machine translation of Kanbara et al. JP 05-093711 A, application published Apr. 16, 1993.*

Chen et al., "A Prototype Two-Dimensional Capillary Electrophoresis System Fabricated in Poly(dimethylsiloxane)", Anal. Chem. 74:1772-1778 (2002).

Li et al., "Integration of Isoelectric Focusing with Parallel Sodium Dodecyl Sulfate Gel Electrophoresis for Multidimensional Protein Separations in a Plastic Microfludic Network", Anal. Chem., Nov. 20, 2003.

Macounova et al., "Generation of Natural pH Gradients in Microfluidic Channels for Use in Isoelectric Focusing", Anal. Chem., 72(16):3745-3751 (2000).

Tan et al., "Miniaturized capillary isoelectric focusing in plastic microfluidic devices", Electrophoresis 23:3638-3645 (2002).

Yao et al., "SDS capillary gel electrophoresis of proteins in microfabricated channels", Proc. Natl. Acad. Sci. USA 96:5372-5377 (1999).

* cited by examiner

*Primary Examiner*—Alex Noguerola
(74) *Attorney, Agent, or Firm*—McKee, Voorhees & Sease, P.L.C.

(57) ABSTRACT

A multiplexed, absorbance-based microfabricated chip electrophoresis system, microfabricated chip, and method of use are included for the detection and identification of protein species. The microfabricated chip electrophoresis system capable of analyzing multiple samples simultaneously. The system uses a microfabricated chip having a sample chamber for first dimension separation of a sample, a first planar array of channels for second dimension separation of the sample approximately perpendicular the sample chamber, and a barrier separating the sample chamber from the first planar array of channels during the first dimension separation. In use, the sample is placed into a sample chamber, a barrier is established around the sample chamber, the sample is isoelectric focused within the sample chamber, the barrier is then removed, and the sample separated in the first array of channels by molecular weight.

28 Claims, 12 Drawing Sheets

MICROFABRICATED CHIP AND METHOD OF USE

TECHNICAL FIELD OF THE INVENTION

This invention relates generally to a multiplexed, absorbance-based electrophoresis system. Specifically, the invention relates to a microfabricated chip utilized in a multiplexed absorbance-based electrophoresis system and a method of using the microfabricated chip in proteomics study.

BACKGROUND OF THE INVENTION

The completion of Human Genome Project has opened the door to a flood of postgenomic applications that rely on genomic sequences. However DNA sequence information alone is not able to predict gene expressions, co- and post-translational modifications and phenotype or multigenic phenomena such as drug administration, cell cycle, oncogene, aging, stress and disease. The understanding of probably half a million human proteins and their relationship to physiological or disease conditions is still a long way away. Proteome is a new fundamental concept, which has recently emerged, that should play a significant role in the battle to unravel biochemical and physiological mechanism of complex multivariate diseases at the functional molecular level. Proteomics can be defined as the qualitative and quantitative comparison of proteomes under different conditions to further unravel biological processes. Proteomics is becoming an important topic in the effort to understand gene regulations and the changes in protein profiles in cellular systems either in physiological conditions or disease conditions. Although still in its infancy, proteomics already promises revolutionary changes in biological and medical sciences.

Proteome studies have developed and continue to be dependent upon the core technology of multidimensional separation techniques, such as 2-D gel electrophoresis (2-DE), and more recently, combined chromatography techniques (e.g. LC-LC). Despite the increased popularity of the latter, 2-D gel electrophoresis remains one of the most frequently chosen methods of choice due to its ability to separate complex mixtures of proteins and to follow multigenic phenomena at the level of whole cells, tissue, and even whole organisms.

2-DE is a method for the separation and identification of proteins in a sample by displacement in 2 dimensions oriented at right angles to one another. Isoelectric focusing (IEF) is used in the first dimension, which separates proteins according to their isoelectric points (pIs). The pI is the pH at which an amphoteric substance is neutral charged. When pH is higher than the pI of a substance, it will be negative charged and vise versa. When a protein is placed in a medium with a pH gradient and subjected to an electric field, it will initially move toward the electrode with the opposite charge. As it migrates, its net charge and mobility will decrease and the protein will slow down. Eventually, the protein will arrive at the point in the pH gradient equal to its pI, where it becomes neutral and stop migrating. If the protein should happen to diffuse to a region of lower (higher) pH, it will become positively (negatively) charged and be forced back toward the cathode (anode) by the electric field. In this way, proteins are focused into sharp bands in the pH gradient at their individual characteristic pI values. SDS-PAGE (sodium dodecyl sulfate-polyacrylamide gel electrophoresis) is the method for the second dimension separation, in which protein separation is based on molecular weight. SDS binds to all proteins, and the net effect is that proteins migrate with a uniform negative charge-to-mass ratio. The pores of polyacrylamide gel sieve proteins according to size (i.e. molecular weight). Smaller proteins move faster through the gel under the electric field than larger proteins, thus achieve molecular sieving. Compared to 1-D electrophoresis based separation methods, 2-D strategy allows the sample to separate over a larger area, increasing the resolution of each component. E.g. unlike PAGE 1-D separation, which can only separate about 100 bands, 2-D gel based separations can analyze samples with much higher complexity (e.g. common 2-D runs can separate thousands of spots).

When first developed, 2-DE utilized carrier ampholyte (CA) to generate pH gradient for the first dimension IEF separation. However there are many disadvantages associated with CA-IEF. Firstly, equilibrium CA-IEF cannot be achieved because of cathodic drift, which means that pH gradient moves towards the cathode end with prolonged focusing time. Secondly, reproducibility of pH gradient is also influenced by the batch-to-batch variability of CA preparations, and by the sources where the CA is obtained. Therefore, the exchange of 2-D gel data between laboratories has been a major problem because of spatial irreproducibility between 2-D gels generated by the CA-IEF. The problems of pH gradient instability and irreproducibility were solved by the introduction of immobilize pH gradient (IPG) for IEF. Certain chemicals, co-polymerized with the acrylamide matrix, generate a much stable pH gradient. The advantages of IPG include the elimination of cathodic drift, an enhancement in reproducibility. Also, the introduction of IPG has greatly improved resolution, especially with the usage of narrow-range IPGs. This advancement makes 2-D gel electrophoresis a core technology of proteome analysis, facilitating spot identification by peptide fingerprinting, amino acid composition, analysis peptide sequencing and mass spectrometry analysis.

However, there are still many disadvantages in this 2-DE technique, which may limit its usage in proteomics researches. The disadvantages of 2D gel electrophoresis include labor-intensive (sample treatment, gel preparing, staining), time consuming (usually takes multiple days to complete one analysis), and not readily automated (need constant human attention). Low throughput is another important factor influencing the cost effectiveness of conventional approaches to proteome analysis. Despite numerous refinements in electrophoretic techniques over the past decade, the above disadvantages associated with the 2-D gel electrophoresis still exist. The process is still tedious and inefficient and the time required to prepare, load, separate and visualize complex mixtures of proteins on conventional 2-D gels is still substantial. To meet the needs of proteomic research, new technologies still need to be developed with the following features: 1) must have increased resolving power; 2) must have higher sensitivity and speed; 3) must be automated and easy to use; 4) must have the ability to perform high throughput analysis and 5) better have the potential to couple with some other techniques such as MS.

Improvements in speed, sensitivity, resolution and automation can be achieved by using capillary electrophoresis (CE), which offers many advantages over traditional gel electrophoresis for the separation of a wide variety of molecules. Multiplexed capillary electrophoresis, which utilizes parallel capillary tubes simultaneously, also provides enhanced throughput. CE on microchips is an emerging new technology that promises to lead the next revolution in chemical analysis. Over the past decade, the field of microfabrication of analytical devices has grown from an esoteric technique to a recognized technique with commercially available systems.

It has the potential to simultaneously assay hundreds of samples in a short time, and also is easier to interface with MS than traditional CE. Isoelectric focusing on microfabricated devices using either natural pH gradient (Analytical Chemistry, 2000, 72, 3745-3751) or ampholyte-generated pH gradient (Electrophoresis, 2002, 23, 3638-3645) has been reported. These resemble the first dimension separation in traditional 2-D gel electrophoresis. On the other hand, efforts have been made to separate proteins based on their sizes in microfludic channels (Proc. Natl. Acad. Sci. USA, 1999, 96, 5372-5377). However these applications are based on single-channel devices, and therefore only provide 1-D separation. Whitesides et al. have constructed a chip device by PDMS (polydimethylsiloxane), on which 2D gel electrophoresis has performed (Analytical Chemistry, 2002, 74, 1772-1778). The first dimension is isoelectric focusing and the second dimension is SDS gel electrophoresis. However, this device is not automated in part because after the first dimension separation, the device has to be manually dissembled and then re-assembled to physically connect the first dimension to the second dimension channels.

These above-mentioned microchip-based studies used fluorescence detection, which required labeling of the protein with dyes, which will change the properties of the sample (e.g. pI and molecular weight). UV (ultraviolet) absorption detection is more useful because of its ease of implementation and wider applicability, especially for the deep-UV (200-220 nm) detection of organic and biologically important compounds. In a UV detection system, a section of capillary tube or microfabricated channel is irradiated with a UV light source. A photodetector detects the light that passes through the tube. When a UV absorbing sample component passes through the irradiated portion of the capillary tube, the photodetector detects less passed light (indicating absorbance). In this way an electropherogram, a plot of absorbance versus time, can be produced. Photodiode arrays (PDA) are used in many commercial CE and HPLC (high performance liquid chromatography) systems for providing absorption spectra of the analytes in real time. Transmitted light from a single point in a flow stream is dispersed by a grating and recorded across a linear array. Yeung et al., in PCT Application WO 01/18528A1, disclosed a multiplexed, absorbance-based capillary electrophoresis system for analyzing multiple samples simultaneously. The use of UV absorbance eliminates the need for protein staining, which is a major contributor for the long time used in traditional 2-D gel electrophoresis.

The primary objective of this invention is to fulfill the above described needs in proteomics study with an improved multiplexed, absorbance-based system.

A further objective is an automated alternative for the 2-D gel electrophoresis, which will provide higher speed, higher sensitivity, higher resolution and higher throughput.

A still further objective is a chip-based microfludic device that at one dimension can perform isoelectric focusing, and at another dimension can perform size-based protein separation.

A still further objective is to include separation mechanisms and the type of information recorded similar to 2-D gel electrophoresis. A still further objective is to include UV absorbance detection.

One or more of these and/or other objectives will become apparent from the specification and claims that follow.

SUMMARY OF THE INVENTION

According to one aspect of the invention, a microfabricated chip electrophoresis system is capable of analyzing complex protein samples. The system comprises a microfabricated chip having a body with a sample chamber, a first planar array of channels longitudinally, and a barrier separating the sample chamber from the first planar array of channels. The system including a photodetector for detecting light passing through the channels and a light source positioned with respect to the photodetector.

According to another aspect of the present invention, a microfabricated chip facilitates analysis of complex protein samples. The microfabricated chip has a sample chamber for first dimension separation of a sample. The microfabricated chip includes a microfabricated chip body having a first planar array of channels longitudinally adjacent and approximately perpendicular the sample chamber and a barrier separating the sample chamber from the first planar array of channels during first dimension separation. The microfabricated chip has a first electrical field generator located adjacent upon the sample chamber and a second electrical field generator adjacent the first planar array of channels adapted for separating a sample by molecular weight.

According to another aspect of the invention, a method of using a multiplexed, absorbance-based microfabricated chip electrophoresis system is provided. The method involves the step of filling a sample chamber with sample to be treated by isoelectric focusing and then establishing a barrier about the sample chamber. The method also has the steps of isoelectric focusing within the sample supplying chamber, avoiding the barrier and then drawing the sample into a first array of channels. The method still further has the step of emitting light from a light source through the first array of channels and then detecting light from the light source with a photodetector.

DETAILED DESCRIPTION OF EXEMPLARY EMBODIMENTS OF THE INVENTION

The invention, as hereinbefore explained, is a microfabricated chip in use with a multiplexed, absorbance-based electrophoresis system. The invention system and method are for the separation, detection and identification of protein species.

By "chip" the applicants mean a discrete piece of material processed to have specialized electrical, chemical, and/or mechanical characteristics upon a plurality of samples. By "microfabricated" the applicants refer to structural elements or features of a device, which have at least one fabricated dimension in the range of from about 0.1 µm to about 500 µm.

Figure 1:
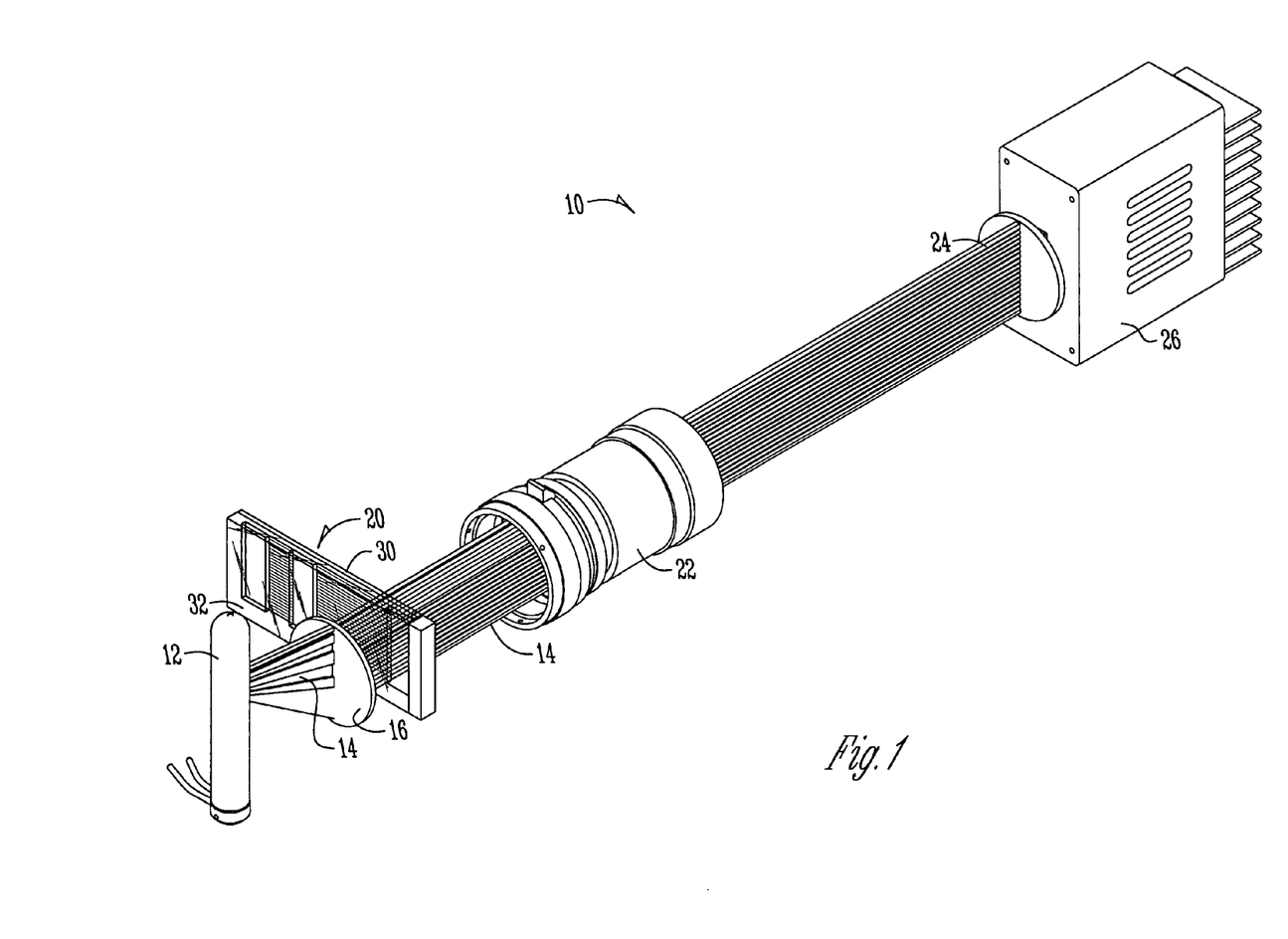
FIG. 1 presents a perspective view of the absorbance-based microfabricated chip electrophoresis system.
Figure 2:
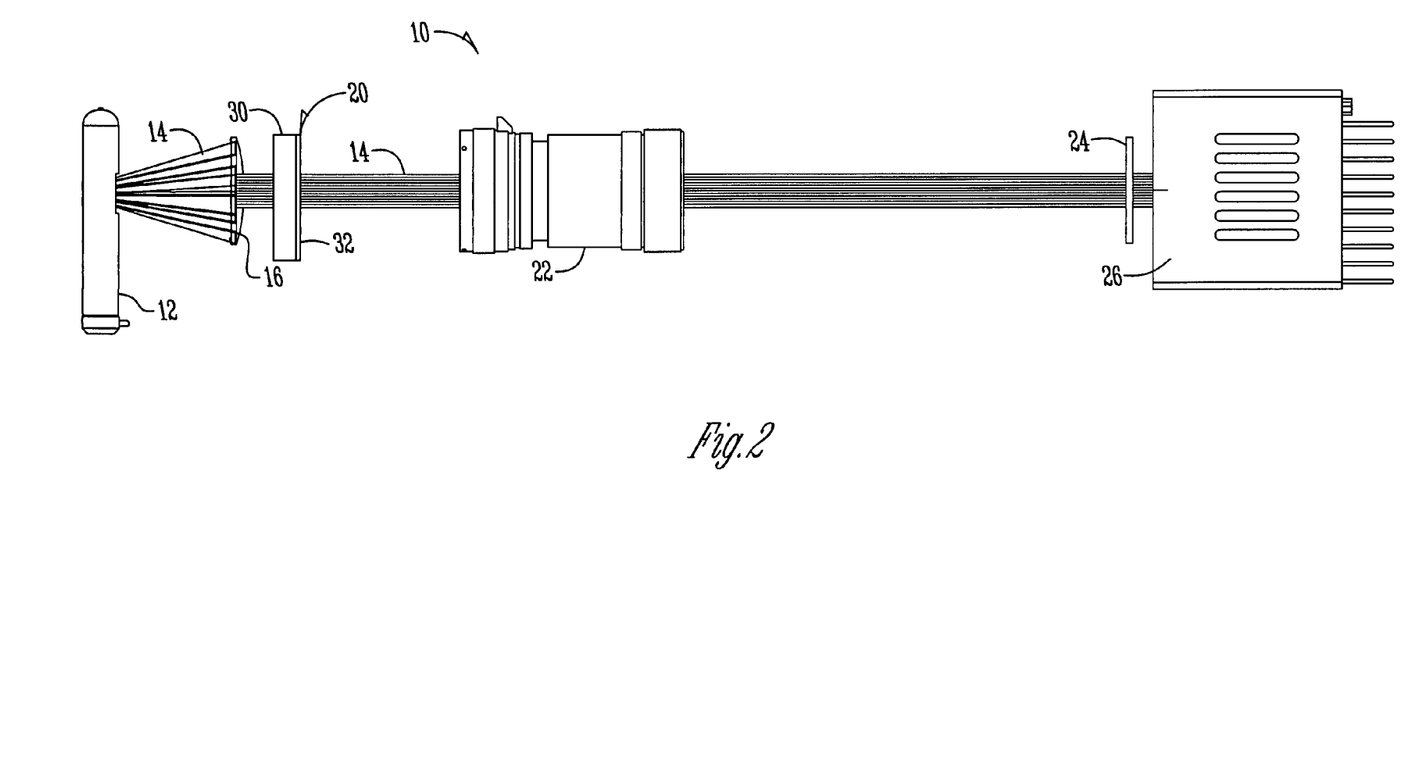
FIG. 2 presents a side view of a light source positioned upon a microfabricated chip and a detector.

Referring to FIG. 1 and FIG. 2, numeral 10 designates the absorbance-based electrophoresis system. The light beam 14 originates in the light source 12 and then travels through the collimating lens 16, the microfabricated chip 20, the flat-field lens 22, the optical filter 24 and is collected in the detector 26.

The distance between the area where light is emitted from the light source 12 and the microfabricated chip 20 is not critical to the practice of the present invention. However, the shorter the distance between the area where light is emitted from the light source 12 and the microfabricated chip 20, the more light is received by the microfabricated chip 20. The more light that the microfabricated chip 20 receives, the more sensitive is the detection. The greater the distance between the area where light is emitted from the light source 12 and the microfabricated chip 20, the more uniform is the light received by the microfabricated chip 20.

Preferably, the distance between the microfabricated chip 20 and the detector 26 is such that the entire array is visible and in focus. FIG. 2 shows a side view of light emitted from the light source 12.

Figure 3:
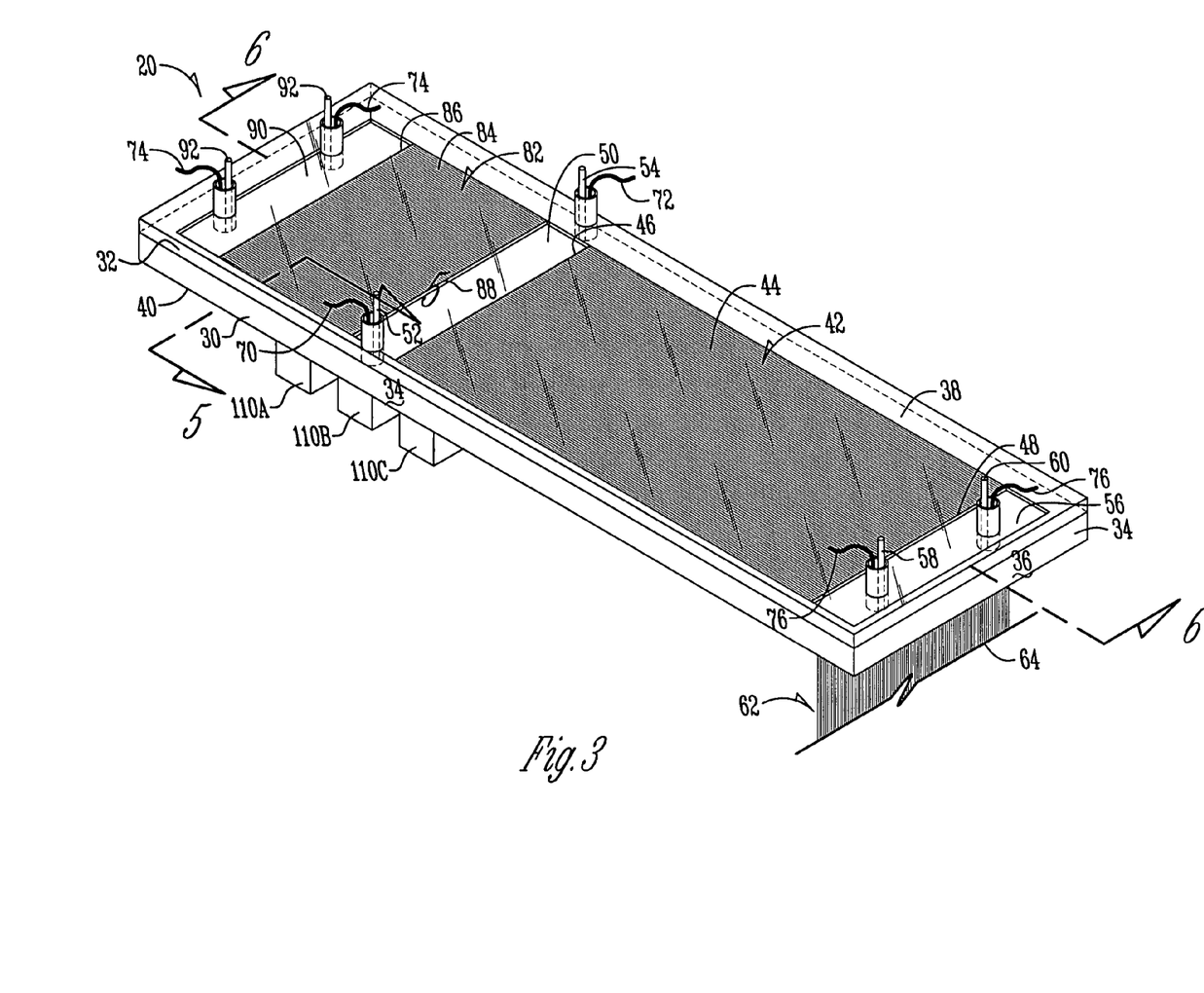
FIG. 3 presents a perspective view of a microfabricated chip of the present invention.

As seen in FIG. 3, the microfabricated chip 20 has a body 30 and a cover 32. The body and the cover are attached together by thermal bonding and/or other bonding techniques such as epoxy bonding. The body 30 has opposing longitudinal sides 34 and opposing lateral sides 36. The body 30 also has a top side 38 and a bottom side 40.

Preferred materials for the microfabricated chip body 30 and cover 32 include, but are not limited to, plastics, poly(dimethylsiloxane) PDMS, quartz or fused silica, glass and other non-conductive materials. The microfabricated channels and chambers may be formed upon the microfabricated chip body 30 by a variety of processing techniques including photolithography, wet chemical etching, laser ablation, air abrasion techniques, injection molding, embossing, and other techniques.

When using a PDMS-quartz approach, the bonding between PDMS and quartz uses an $O_2$ plasma treatment. The method of bonding the PDMS to quartz is to treat the substrates in an $O_2$ plasma at 30 watts for 60 seconds before bringing them into contact and then carefully bringing them into contact to avoid trapping air in-between the substrates. The PDMS-quartz product is then annealed in a 60° C. oven for ten minutes to accelerate an irreversible bond between the PDMS and quartz. Holes can then be cut into the PDMS film to gain access to the chambers and channels. Connectors can be glued to cover the holes so that easy connections to external devices such as pumps, valves or syringes can be made.

Figure 4:
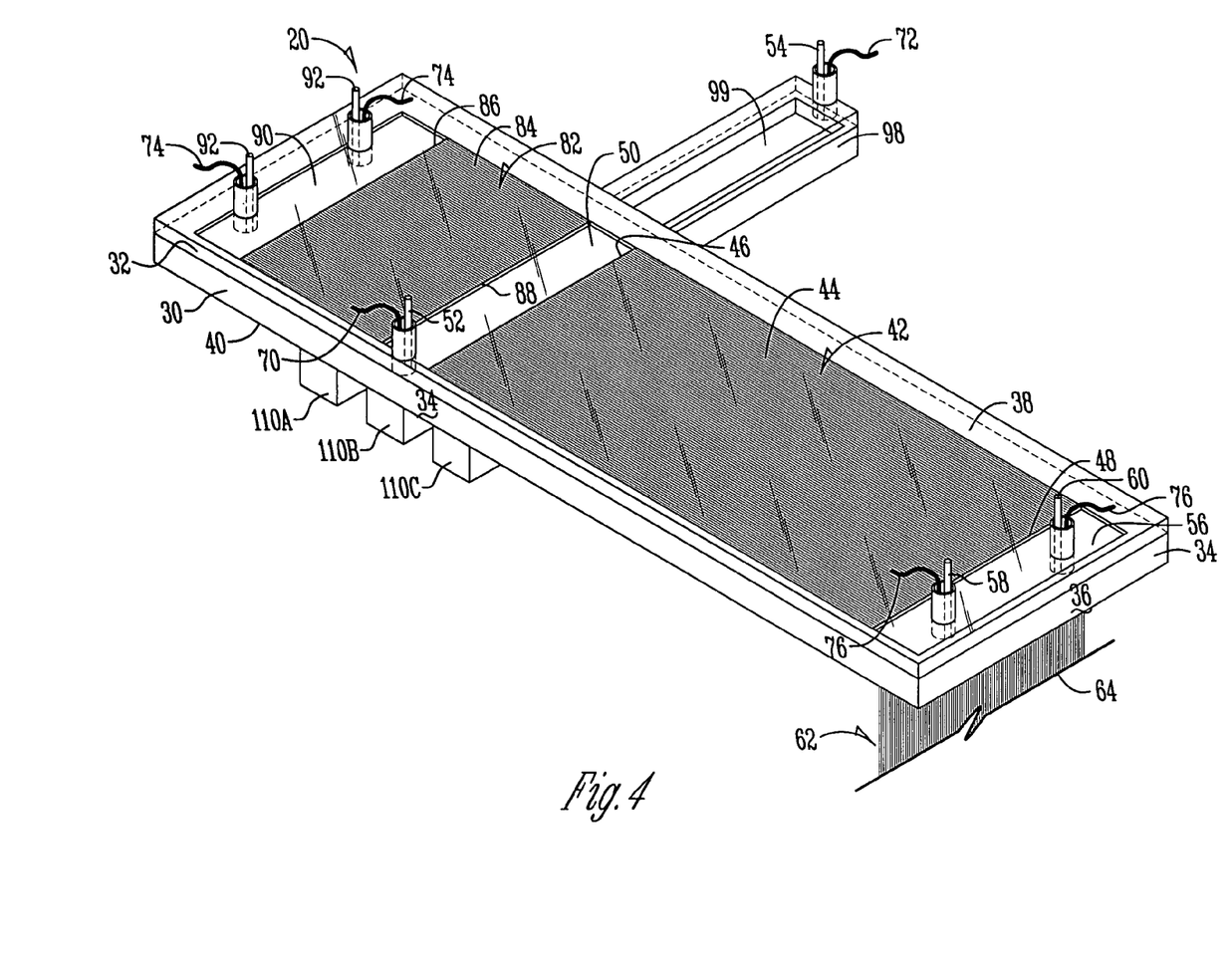
FIG. 4 presents a perspective view of the microfabricated chip with an extended sample chamber.

As seen in FIG. 4, upon the top side 38 of the body 30 is a first planar array of channels 42 made up of individual first channel 44. The first channels 42 have first channels inlet end 46 and first channels outlet end 48.

By "channels" 42 is meant more than one, preferably at least about 10, more preferably at least about 90, and desirably as many as can be accommodated by the system described herein. The microfabricated chip 20 allows the passage of light from the light source 12 through the microfabricated chip body 30 facing the light source 12, through the samples in the channels 42, and through the microfabricated chip cover 32 facing the detector 26. Thus, the microfabricated body 30 and cover 32 are desirably transparent, although, in some instances, the microfabricated body 30 and cover 32 can be translucent. It is not necessary for the entirety of the microfabricated body 30 and cover 32 to allow the passage of light from the light source 12 as described above as long as at least a portion allows the passage of light from the light source 12 such that the samples in the first planar array of channels 42 are irradiated and light that is not absorbed by the absorbing species and the samples is detectable by the detector 26.

In general, the channels 42 defined by the body 30 should have smooth surfaces. The cross-section of the channels 42 is not critical to the present invention. However, the smaller the cross-section of the individual channel 44, the more useful is the microfabricated chip 20 in highly multiplexed applications as a greater number of channels 44 can be used in a smaller amount of space.

The body 30 may have longitudinal sides 34 a length between 4 and 30 cm and lateral sides 36 a width between 2 and 10 cm wide. The body 30 should be of sufficient thickness as to maintain the structural integrity of the microfabricated chip 20, yet not so thick as to adversely impede the passage of light through the first channels 42.

Figure 5:
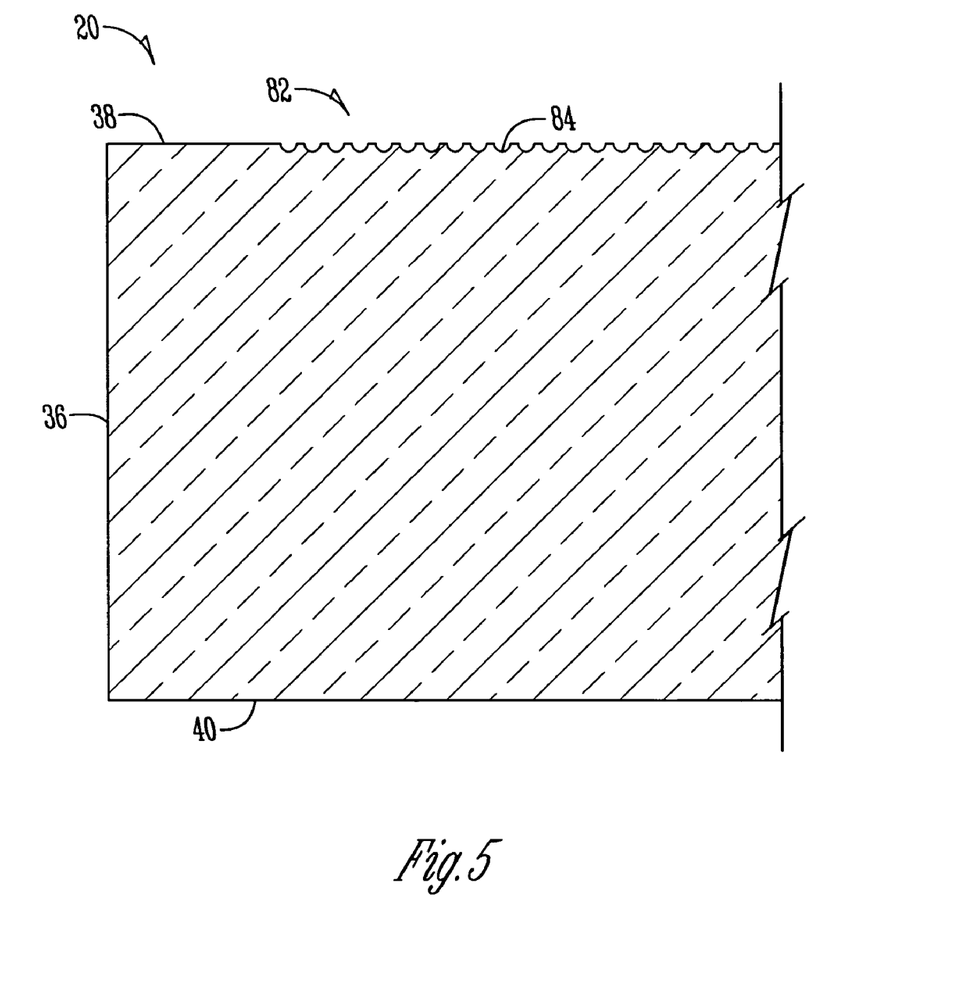
FIG. 5 presents a cross sectional view of FIG. 3 taken along Line 5-5.
Figure 6:
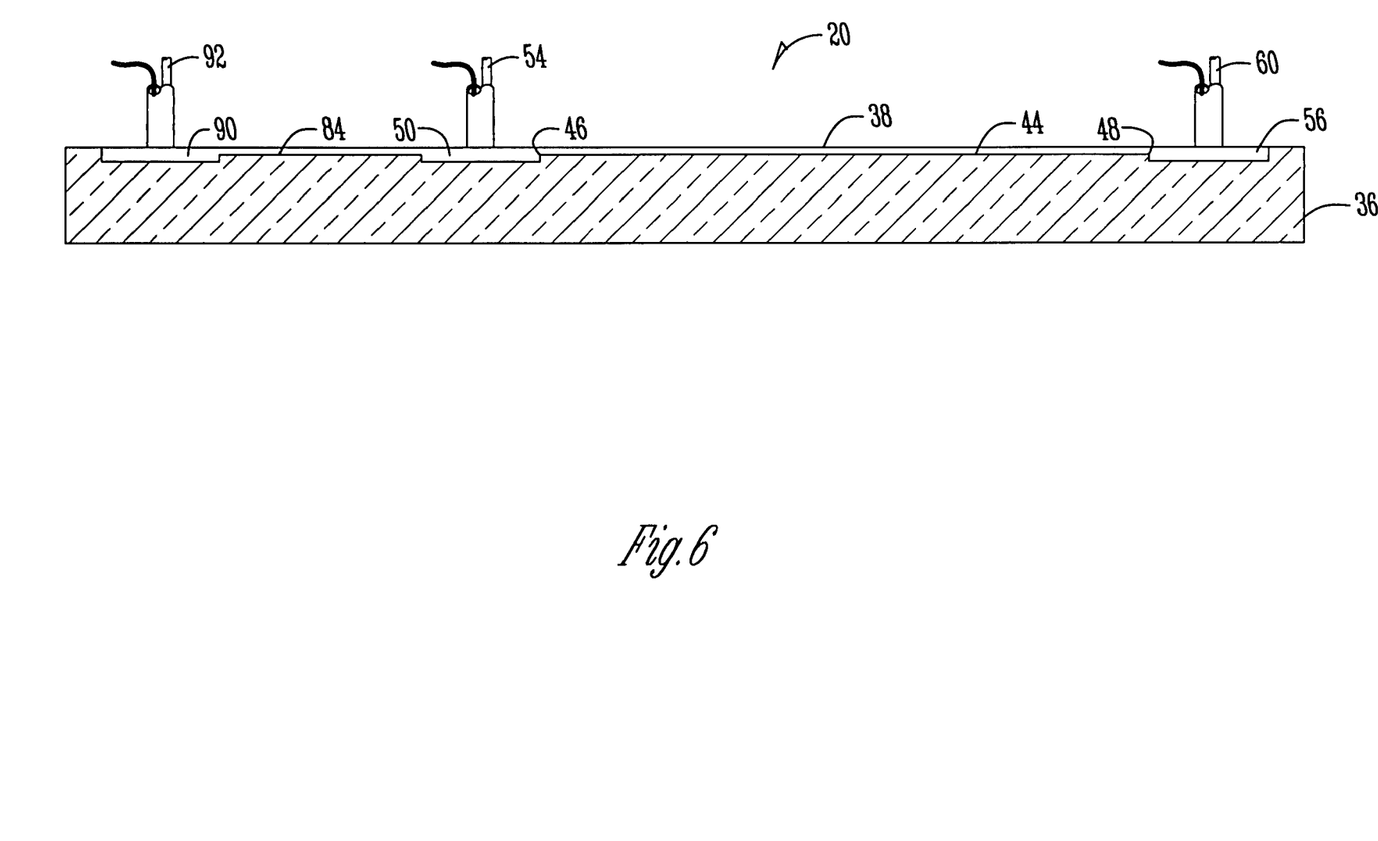
FIG. 6 presents a cross sectional view of FIG. 3 taken along Line 6-6.

As seen in FIGS. 5 and 6, the shape of the first channels 42 is not critical to the present invention. The first channels 42 can have any suitable shape. However, the size of the channel 44 is between 50-200 µm. Desirably, the shape of the channels 20 is conducive to being closely packed and minimizes the generation of stray light. The first channels 42 are from about 5 cm to about 25 cm long.

The channels 44 in the planar array are arranged substantially parallel and adjacent to each other to form the first planar array of channels 42.

As seen in FIG. 3, the top side 38 of the body 30 has a sample chamber or sample channel 50 defined upon the body located approximately lateral to the first planar array of channels inlet end 46. The sample chamber 50 is adapted for isoelectric focusing of the sample and for supplying sample to the first planar array of channels 42. The sample chamber 50 has sample-supplying tubes 52, 54 located upon opposing sides. The sample-supplying tubes 52, 54 pass through the cover 32 of the microfabricated chip 20 and contact the sample chamber 50. The tubes 52, 54 may be made of an inert material such as polytetrafluoroethylene, polyethylene, polypropylene or polyethylene terephthalate, etc.

The microfabricated chip 20 also has a receiving chamber 56 located approximately lateral to the first planar array of channels outlet end 48 and is adapted for aggregately receiving samples from the first array of channels 42. The receiving chamber 56 has tubes 58, 60 that pass through the cover 32 of the microfabricated chip 20 and into the receiving chamber 56. The tubes 58, 60 are made of an inert material such as polytetrafluoroethylene, polyethylene, polypropylene or polyethylene terephthalate, etc. These tubes may be used to supply a gel matrix 66 to the first planar array of channels 42.

An additional array of collection tubes 62 made up of individual collection tubes 64 are positioned within the receiving chamber 56 to collect sample that may be coming from the first planar array of channels 42. The collection tubes may be fine enough to collect individual channel 44 sample. Alternatively, the collection tubes 62 may be wider than individual channels to collect an aggregate of a multiple of channel 44. As seen in FIG. 4, the sample chamber may be extended outside of alignment with the first array of channels 44 by having a physical border 98 defined and extended sample chamber 99. The purpose of the extended chamber is to further enhance resolution of the first dimension IEF separation. By optimizing sample chemistry (i.e. by changing N,N.N',N'-tetramethylethylene diamine, TEMED, concentration in the sample matrix), the proteins can only be focused in the extended sample chamber 99. Since this extended IEF channel 99 has defined walls 98, proteins can be separated with a much higher resolution. Once IEF is finished, the focused protein bands will then be mobilized into sample chamber 50.

Mobilization of the focused bands is critical. Different mobilization methods including hydrodynamic mobilization, EOF (electroosmotic flow)-driving mobilization and electrokinetic mobilization may be used. The first choice is EOF-driving mobilization because no additional modification to the current set-up is necessary. Residual EOF will drive the resolved protein bands from the extended chamber 99 into sample chamber 50 while preserving much of the resolution. The result indicated that EOF is capable to realize mobilization of the focused protein bands.

A gel matrix 66, illustrated in FIGS. 8-9 and 11-12, is within the first array of channels 42. The gel matrix may be made from water-soluble polymers and sodium dodecyl sulfate (SDS) at certain concentrations.

The first electrical field generator has a first terminal 70 and a second terminal 72 located adjacent the supply chamber 50 opposing sides 34 and adapted for separating a sample by isoelectric focusing.

The second electrical field generator has a first terminal 74 and a second terminal 76 located on the lateral sides 36 of the body 30. The first terminal 74 and second terminal 76 in combination are adapted for producing a longitudinal electric field across the microfabricated chip 20.

As seen in FIG. 4, a microfabricated chip 20 may also have a second planar array of channels 82 made up of individual second channel 84. A second planar array of channels 82 has a second channel inlet end 86 and a second channel outlet end 88.

The buffering chamber 90 has buffering supply tubes 92 penetrating the cover 32 entering into the buffering chamber 90. These tubes 92 may be used to supply a buffering solution 104 to the buffering chamber 90. The buffering solution in the buffering chamber fills the second planar array of channels 82. The buffering solution is adapted for supplying SDS to the sample containing proteins after isoelectric focusing.

For illustration purposes in FIGS. 7-9 and 10-12, a sample made up of six components is depicted being separated in the sample-supplying chamber 50. Component 120 has an isoelectric point of pH 3.4 and a medium molecular weight. Component 122 has an isoelectric point of pH 3.5 and large molecular weight. Component 124 has an isoelectric point of 6.2 and a small molecular weight. Component 126 has an isoelectric point of 7.6 and a large molecular weight. Component 128 has an isoelectric point of 8.2 and a medium molecular weight. Component 130 has an isoelectric point of 9.1 and a small molecular weight.

Figure 7:
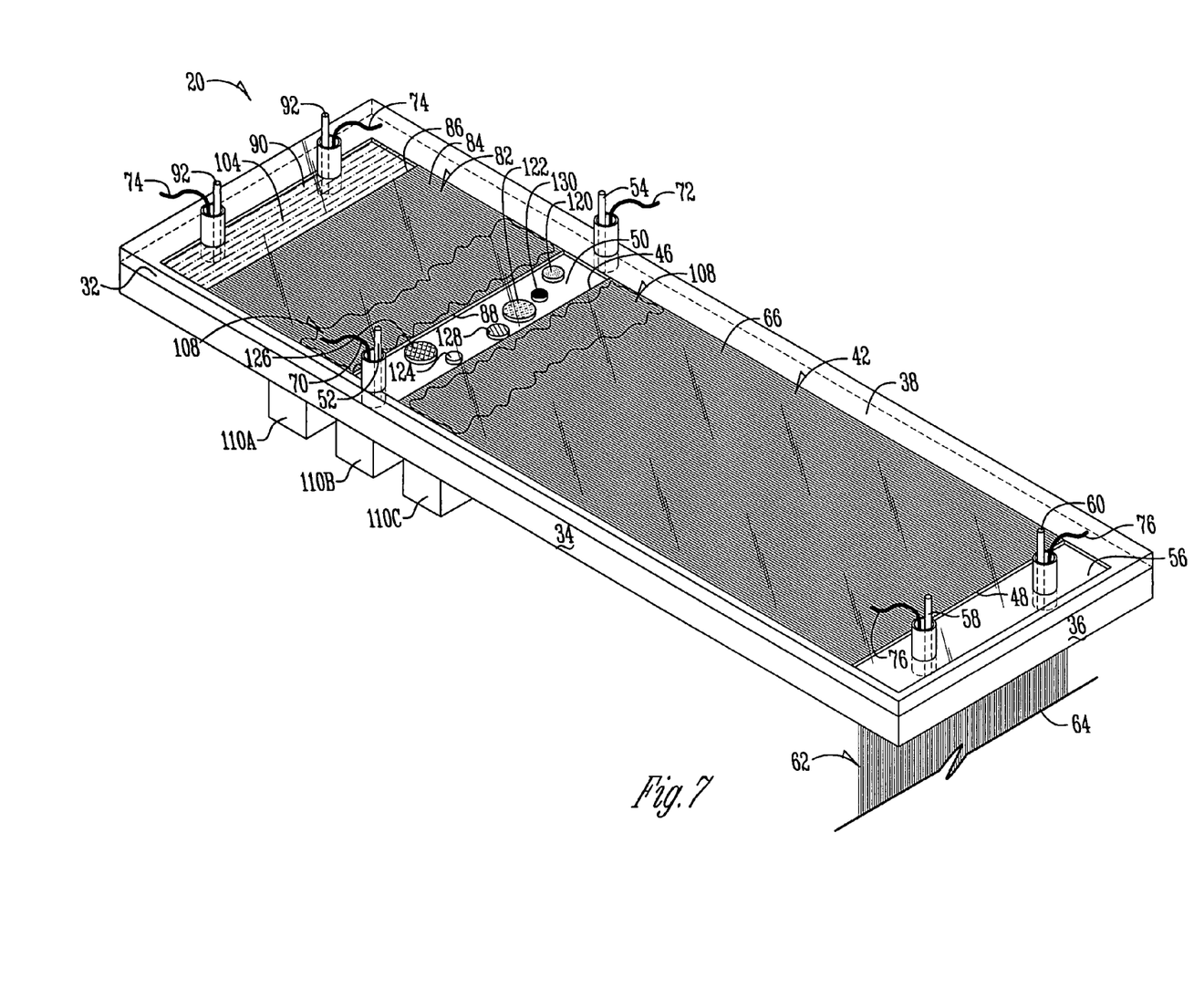
FIG. 7 presents a perspective view of the microfabricated chip having a sample within the sample chamber with six intermixed chemical species.

As seen in FIG. 7, the microfabricated chip may be used in the multiplexed, absorbance-based electrophoresis system. The microfabricated chip 20 is first supplied with a sample 102 as placed into a sample-supplying chamber 50.

Figure 12:
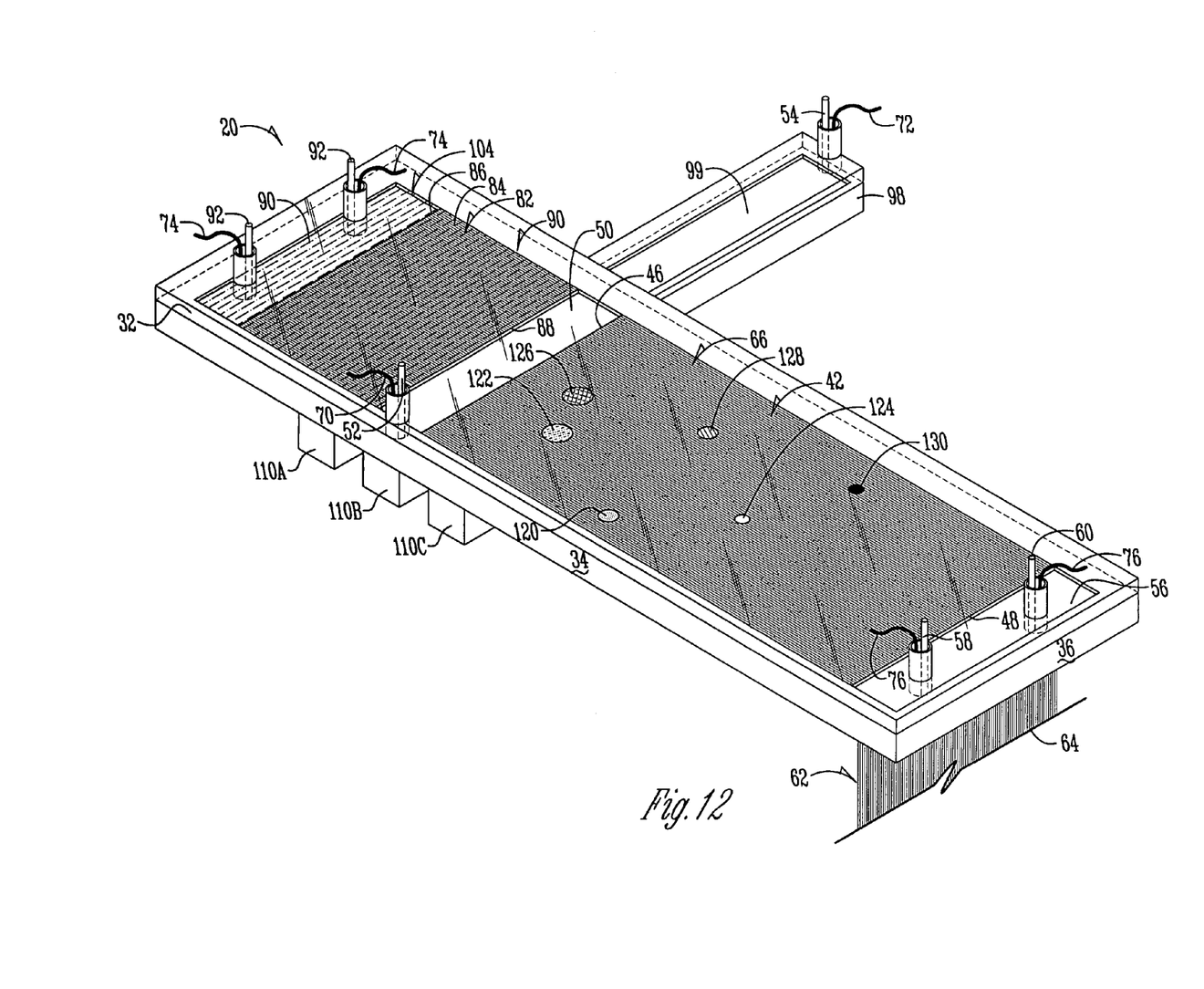
FIG. 12 presents a perspective view of the microfabricated chip with an extended sample chamber having the chemical species sorted by molecular weight.

The sample in the sample-supplying chamber 50 may be used with a carrier ampholyte preferably at 1 to 3%. Using a carrier ampholyte, the pH gradient range for isoelectric focusing is from 3-10 pH. The sample in the sample-supplying chamber 50 may be used with an ampholyte free solution. In an ampholyte free solution, the pH gradient range for isoelectric focusing is from 1-14 pH. FIGS. 7 and 12 depict a microfabricated chip using a carrier ampholyte solution and therefore the range for isoelectric point is 3-10 pH.

Figure 8:
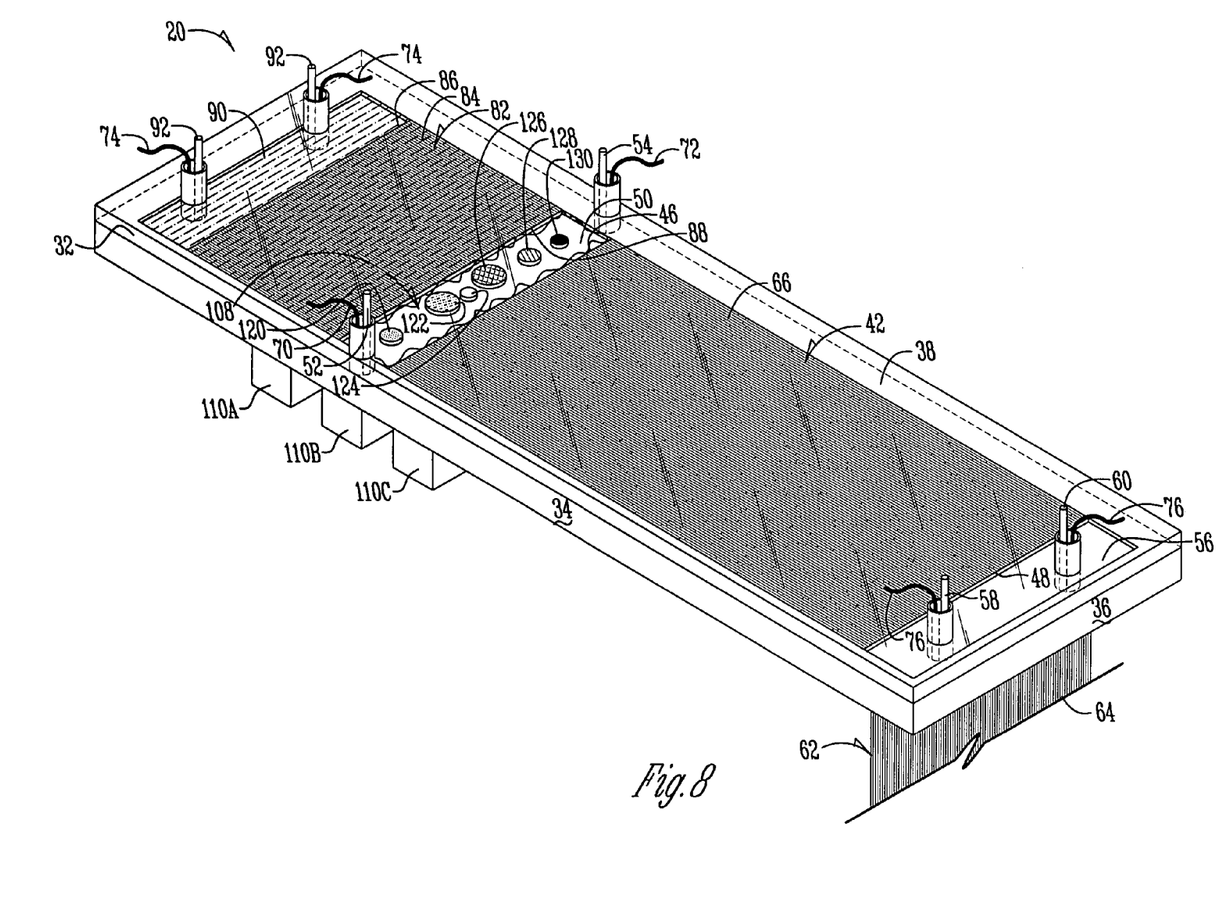
FIG. 8 presents a perspective view of the microfabricated chip having a sample within the sample chamber with the six chemical species isoelectrically focused.
Figure 9:
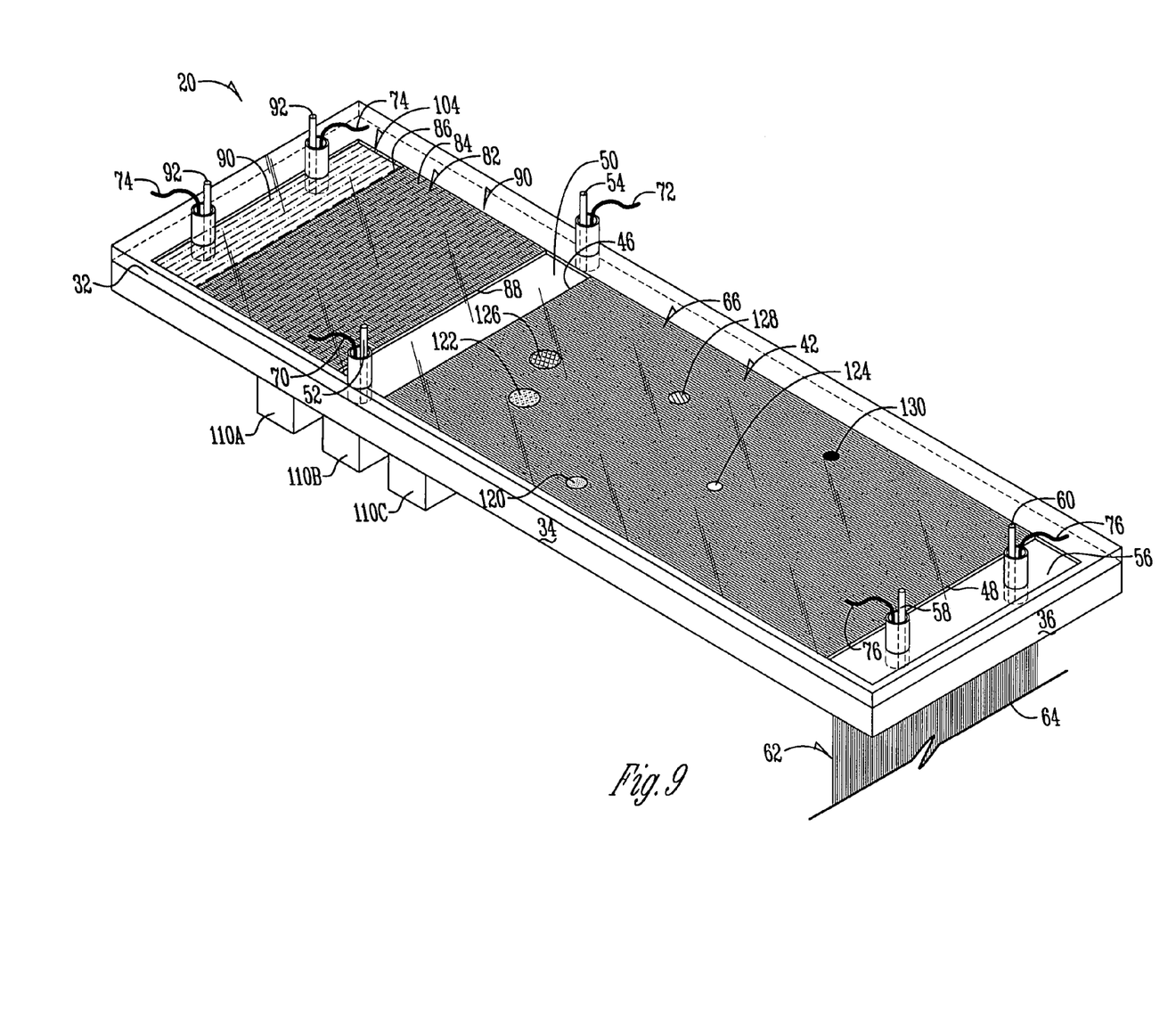
FIG. 9 presents a perspective view of the microfabricated chip having the chemical species sorted by molecular weight.

As seen in FIG. 7, sample 102 is isolated by freezing portions 108 of the first array of channels 42 and the second array of channels 82. The frozen portions 108 significantly decrease the current through the side channels during isoelectric focusing. The frozen portions 108 minimize the diffusion of sample and buffer species that will negatively impact the sample being separated in the sample chamber 50. The thermal electric cooler 110 A-C (TEC) with a water-cooled heat sink may be used to reach temperatures where the buffer freezes. Three TEC devices may be used to freeze different parts of the channels as desired. First, all the channels are filled with SDS-sieving buffer. Prior to sample filling into the IEF channel, TEC1 110A and TEC3 110C are enabled to freeze the second dimension channels, which are positioned on both sides of the sample chamber 50. Then the IEF chamber is filled with the sample solution and the IEF separation is initiated as seen in FIG. 7. The electrical field causes the samples to migrate to the isoelectric point. Once the samples have achieved their isoelectric point they become stationary. After completing the IEF separation, TEC2 110B is enabled to freeze the focus protein bands in a sample chamber 50. Then TEC1 110A and TEC3 110C are disabled and the second dimension channels are thawed while keeping the IEF channel 50 frozen as seen in FIG. 8. The next steps are turning on the high-voltage power supply and thawing the IEF channel 50 so that the focused protein bands can be injected into second dimension channels 42 and get separated as in FIG. 9.

Figure 10:
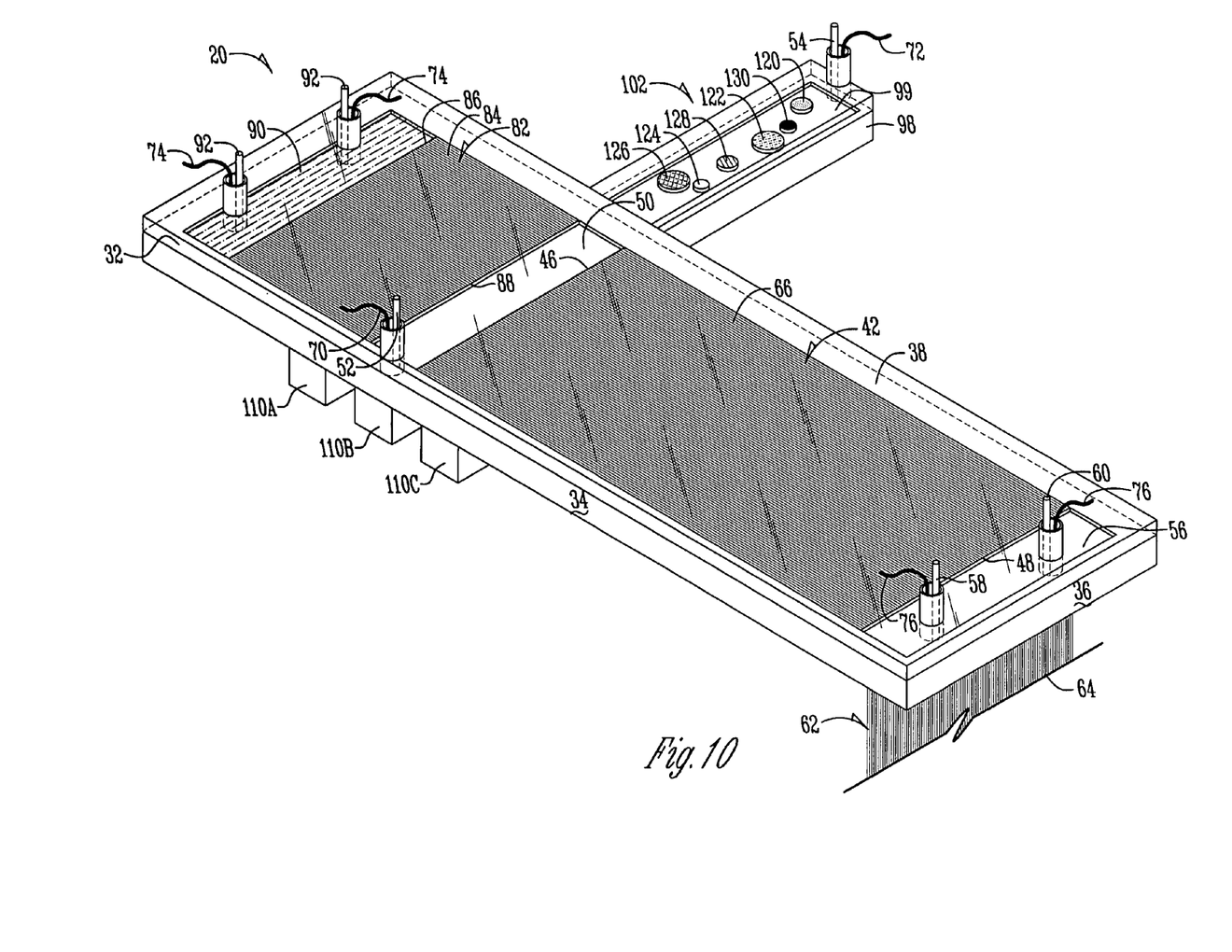
FIG. 10 presents a perspective view of the microfabricated chip with an extended sample chamber having a sample within the sample chamber with six intermixed chemical species.

As seen in FIG. 10, alternatively, an approach to achieving enhanced separation within the sample chamber 50 includes using a chamber extension 99 having a physical border 98. By optimizing sample chemistry (i.e. by changing N,N,N',N'-tetramethylethylene diamine, TEMED, concentration in the sample matrix), the proteins can only be focused in the chamber extension 99 using a first electrical field generator having a first terminal 70 and a second terminal 72. Since this part of IEF channel has defined walls on both sides, proteins can be separated with a much higher resolution. As described previously, TEC1 110A and TEC3 110C is enabled to freeze the second dimensional channels prior to sample filling and IEF separation. The focused protein bands will then be mobilized toward sample chamber 50. By carefully controlling the mobilization process, resolution is expected to be preserved. Once mobilization is finished, TEC2 110B is enabled to freeze the focus protein bands in a sample chamber 50. Then TEC1 110A and TEC3 110C are disabled and the second dimension channels are thawed while keeping the IEF channel 50 frozen. The next steps are turning on the high-voltage power supply and thawing the IEF channel 50 so that the focused protein bands can be injected into second dimension channels 42 and get separated.

The mobilization process includes hydrodynamic mobilization, EOF (electroosmotic flow), and electrokinetic mobilization. As illustrated EOF-driving mobilization is used as no additional modification to the electrical set-up is necessary.

Figure 11:
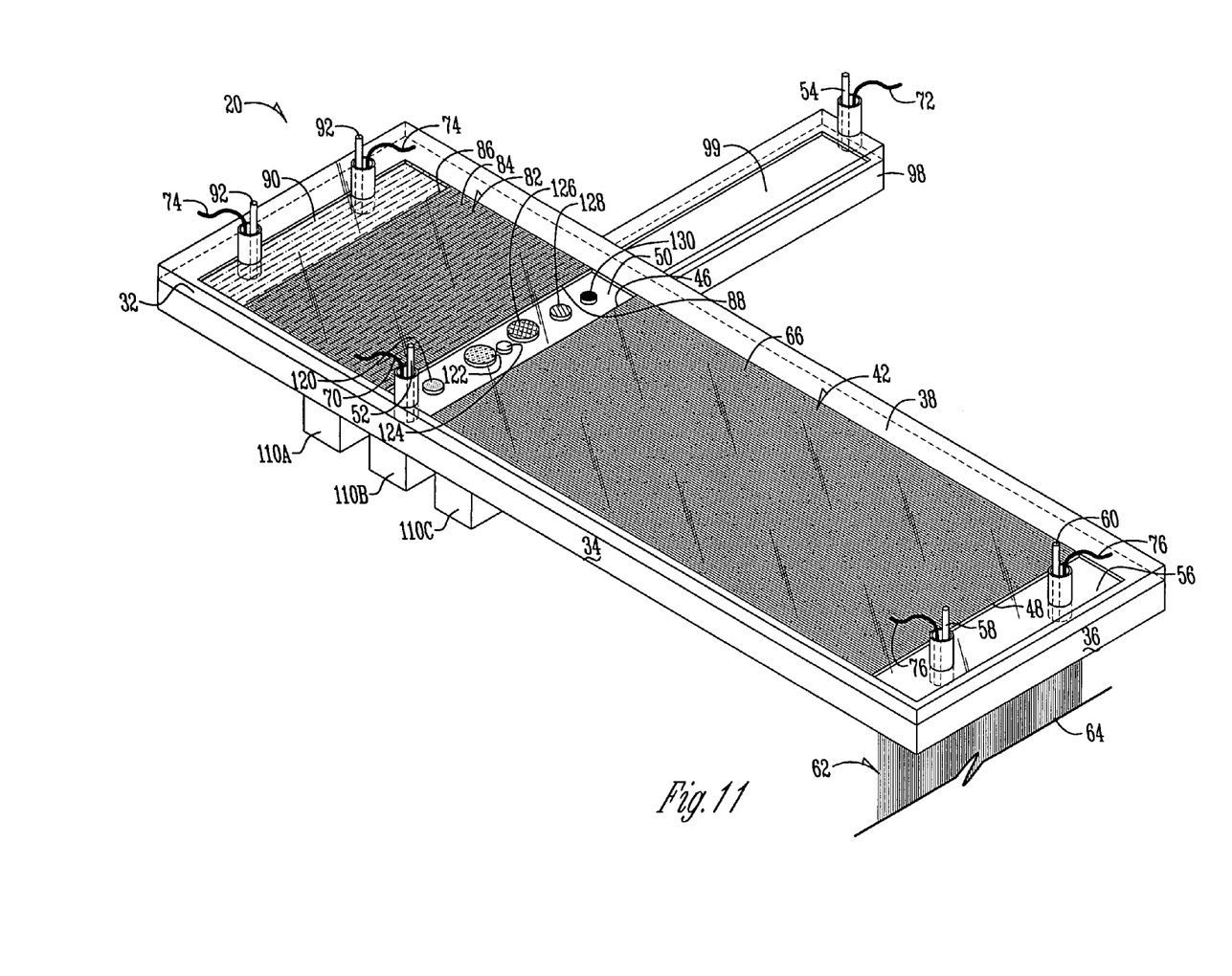
FIG. 11 presents a perspective view of the microfabricated chip with an extended sample chamber having a sample within the sample chamber with the six chemical species isoelectrically focused.

The buffering chamber 90 contains buffering solution 104 with SDS. As seen in FIG. 11, the buffering solution 104 from the chamber 90 fills a second array of planar channels 84 with buffering solution 104. The buffering solution 104 treats the sample 102 within the sample-supplying chamber 50.

As seen in FIG. 12, once the samples have been treated with buffering solution, they possess an electrical charge. This electrical charge allows them to be separated through electrophoresis in an electrical field. The sample when exposed to a gel matrix 66 within a first array of channels may be separated by molecular weight within the first array of channels 42. This separation occurs by use of a second electrical field generator having a first terminal 74 and second terminal 76.

As seen in FIG. 1, as the samples migrate along the first array of channels they pass over a light beam emitted from a light source 12. This light provides the means of detecting sample passing above the source with a photodetector 26. Once sample 102 passes over the light beam 114, it may be then collected in the receiving chamber 56.

The microchip may be reusable. Once the desired sample has passed through, the gel matrix in the first planar array 42 may be flushed out and replaced with new gel matrix. Sample may be re-supplied. Buffering solution may be replaced. The supply and removing of these components may be done through the tubes 52, 54, 58, 60, and 92.

The electrical potential used for isoelectric focusing and electrophoretic separation is not critical to the invention. A typical potential ranges from 5,000 to 30,000 V.

If a large amount of heat is generated during the method, particularly in the vicinity of the planar array of channels 42, cooling should be employed to dissipate the heat. Fans can cool the microfabricated chip 20.

As seen in FIGS. 1 and 2, the detector 26 can comprise any suitable means of detecting absorption. Preferably, the detector 26 comprises a plurality of absorption detection elements, such as a plurality of photosensitive elements, which desirably are positioned in a linear array, although a two-dimensional image array detector can be used. The detector 26 is desirably rigidly mounted to reduce flicker noise.

The light source 12 preferably emits light of a wavelength in the range from about 180 nm to about 1500 nm. Examples of a suitable light source 12 include mercury (for ultra violet (UV) light absorption), tungsten (for visible light absorption), iodine (for UV light absorption), zinc (for UV light absorption) cadmium (for UV light absorption), xenon (for UV light absorption) or deuterium (for UV absorption) lamps. Desirably, the light source 12 emits a wavelength of light that will be absorbed by the species of interest. Which wavelength of light is absorbed by the species of interest can be determined using a standard absorption spectrometer. Alternatively, spectroscopic tables that provide such information are available in the art, such as through the National Institute of Science and Technology. Desirably, a maximally absorbed wavelength of light is selected for a given species to be detected or measured such that smaller amounts of the absorbing species can be detected. The light source 12 can be a point source. Also, preferably, the light source 12 has a power output of about 0.5 mW to about 50 mW.

Preferably, raw data sets are extracted into single-diode electropherograms and analyzed by converting the transmitted light intensities collected at the detector 26 to absorbance values. Alternatively, as many as five and preferably three adjacent diodes may be summed for each channel 44 of the array to increase the overall signal to noise ratio. Mathematical smoothing can be used to reduce noise significantly, without distorting the signal. In this regard, as high a data acquisition rate as possible should be employed to provide more data points for smoothing.

The microfabricated chip 20 avoids the use and disadvantages of capillary tubes as channels are directly formed into the microfabricated chip body 30. Capillary tubes allow the passage of light from the light source 12 through the walls of the capillary tubes facing the light source, through the samples in the capillary tubes, and through the walls of the capillary tubes facing the detector. Thus, forming the channels directly into the body eliminates variations experienced by using light transmitted through capillary tube walls. In general, the capillary tubes have smooth surfaces and uniformly thick walls; however variations in manufacturing may create surfaces that are not smooth and walls varying in thickness. Thus, forming the channels directly into the body eliminates the variations experienced in manufacturing capillary tubes. Capillary tubes come in a variety of cross-sections for holding sample; however, microfabricated channels for holding sample may be formed smaller than the cross-section of capillary tubes and compressed into a tighter formation. The smaller the cross-section for holding sample and the tighter the formation the more useful is a device; thus, the microfabricated chip is more useful than an array of capillary tubes for highly multiplexed applications as a greater number of channels may be used in a smaller amount of space. Typically, the capillary tubes in the planar array are arranged substantially parallel and adjacent to each other; however, slight inconsistencies in capillary wall diameter can prevent them from being in contact along their entire lengths. The microfabricated chip solves this problem by having channels microfabricated directly into the body 30.

The microfabricated chip 20 having all of these above advantages and reduced equipment is more efficient than the previous capillary tube design. This efficiency results in advantages over the capillary tube design such as quicker analysis time, the ability to insert and remove the microfabricated chip as a unit for analysis and potentially by robotics, and the ability to do multiple tests in a smaller more compact area.

In the drawings and specification there has been set forth a preferred embodiment of the invention, and although specific terms are employed, these are used in a generic and descriptive sense only and not for purposes of limitation. Changes in the form and the proportion of parts as well as in the substitution of equivalents are contemplated as circumstances may suggest or render expedient without departing from the spirit or scope of the invention as further defined in the following claims.

What is claimed is:

1. A multiplexed, absorbance-based microfabricated chip electrophoresis system comprising:
   a microfabricated chip having:
   a sample chamber for first dimension separation of a sample,
   a first planar array of channels having outlet ends for second dimension separation of the sample, the first planar array of channels approximately perpendicular the sample chamber,
   a receiving chamber approximately lateral to the first planar array of channel outlet ends and an array of collection tubes affixed to the receiving chamber and in matching alignment with the planar array of channels for aggregately receiving samples from said channels,
   a barrier separating the sample chamber from the first planar array of channels during first dimension separation;
   a photodetector for detecting light passing through the first planar array of channels; and
   a light source positioned with respect to the photodetector.

2. The system of claim 1 wherein the microfabricated chip further comprises a gel matrix within the planar array of channels.

3. The system of claim 1 further comprising an electrical field generator located about the microfabricated chip body adapted for producing an electrical field for moving sample through the channels.

4. The system of claim 1 wherein the microfabricated chip body is transparent over the range of wavelengths of light absorbed by a sample.

5. The system of claim 1 wherein the microfabricated chip first planar array of channels comprises at least about 10 channels.

6. The system of claim 1 wherein the microfabricated chip first planar array of channels comprises at least about 90 channels.

7. The system of claim 1 wherein the microfabricated chip channels are at least 50 micron wide.

8. The system of claim 1 wherein the microfabricated chip channels are at least 200 micron wide.

9. The system of claim 1 wherein the photodetector is a linear photodiode array.

10. The system of claim 1 wherein the light source emits light of a wavelength between 180 nm to about 1500 nm.

11. The system of claim 1 wherein the light source has a power output of about 0.5 mW to about 50 mW.

12. The system of claim 1 which further comprises an optical filter positioned between the planar array of channels and the photodetector.

13. The system of claim 1 which further comprises a flat-field lens positioned between said planar array of multiple channels and the photodetector.

14. The system of claim 1 which further comprises a collimating lens positioned between the light source and the planar array of channels.

15. A microfabricated chip for use with an absorbance-based electrophoresis system which analyzes multiple samples, the microfabricated chip comprising:
   a sample chamber for first dimension separation of a sample;
   a first planar array of channels having outlet ends for second dimension separation of the sample, the first planar array of channels positioned adjacent and approximately perpendicular the sample chamber;
   a receiving chamber approximately lateral to the first planar array of channel outlet ends and an array of collection tubes affixed to the receiving chamber and in matching alignment with the planar array of channels for aggregately receiving samples from said channels,
   a barrier separating the sample chamber from the first planar array of channels during first dimension separation;
   a first electrical field generator located adjacent the sample chamber;
   a second electrical field generator located adjacent the first planar array of channels.

16. The microfabricated chip of claim 15 further comprising a second planar array of channels positioned adjacent the sample supplying chamber.

17. The microfabricated chip of claim 16 further comprising a buffering chamber approximately adjacent to the second planar array of channels.

18. The microfabricated chip of claim 17 further comprising a gel matrix within the first planar array of channels.

19. The microfabricated chip of claim 18 further comprising a buffering solution within the second planar array of channels adapted for supplying an electrical charge to a sample containing proteins after isoelectric focusing.

20. The microfabricated chip of claim 15 wherein the first planar array of channels has a length between 2 to 25 cm.

21. The microfabricated chip of claim 15 wherein the first planar array of channels comprises at least about 90 channels.

22. The microfabricated chip of claim 15 wherein the sample chamber extends beyond the planar array of channels to define a portion of the sample chamber.

23. The microfabricated chip of claim 22 wherein the sample chamber contains an optimized sample matrix that permits proteins in the sample to be isoelectrically focused in the portion.

24. The microfabricated chip of claim 23 wherein the sample may be moved from the portion into the sample chamber in alignment with the first planar array of channels through electroosmotic flow driving mobilization.

25. The microfabricated chip of claim 23 wherein the sample may be moved from the portion into the sample chamber in alignment with the first planar array of channels through electrokinetic mobilization.

26. The microfabricated chip of claim 23 wherein the sample may be moved from the portion into the sample chamber in alignment with the first planar array of channels through hydrodynamic mobilization.

27. The microfabricated chip of claim 15 wherein the barrier reduces the current between sample chamber and the first planar array of channels during isoelectric focusing.

28. The microfabricated chip of claim 27 wherein the barrier is a frozen area of the first planar array of channels.

* * * * *